United States Patent
Carpenter, II et al.

(10) Patent No.: US 7,847,941 B2
(45) Date of Patent: Dec. 7, 2010

(54) FIBER OPTICAL ASSEMBLY FOR FLUORESCENCE SPECTROMETRY

(75) Inventors: Robert W. Carpenter, II, Pagosa Springs, CO (US); Richard Rubenstein, Staten Island, NY (US); Martin Piltch, Los Alamos, NM (US); Perry Gray, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 920 days.

(21) Appl. No.: 11/634,546

(22) Filed: Dec. 5, 2006

(65) Prior Publication Data

US 2007/0139652 A1 Jun. 21, 2007

Related U.S. Application Data

(60) Provisional application No. 60/748,523, filed on Dec. 7, 2005.

(51) Int. Cl.
*G01N 21/25* (2006.01)
(52) U.S. Cl. .................................................. 356/417
(58) Field of Classification Search ......... 356/317–318, 356/417
See application file for complete search history.

(56) References Cited

U.S. PATENT DOCUMENTS

| | | | | |
|---|---|---|---|---|
| 4,702,598 A | * | 10/1987 | Bohmer | 356/417 |
| 6,124,597 A | * | 9/2000 | Shehada et al. | 250/461.2 |
| 6,538,735 B1 | * | 3/2003 | Duebendorfer et al. | 356/318 |
| 2002/0001075 A1 | * | 1/2002 | Tsien et al. | 356/72 |
| 2003/0116436 A1 | * | 6/2003 | Amirkhanian et al. | 204/452 |

* cited by examiner

*Primary Examiner*—Kara E Geisel
(74) *Attorney, Agent, or Firm*—Mark N. Fitzgerald; Robert P. Santandrea; Juliet A. Jones

(57) ABSTRACT

A system for analyzing a sample for the presence of an analyte in a sample. The system includes a sample holder for containing the sample; an excitation source, such as a laser, and at least one linear array radially disposed about the sample holder. Radiation from the excitation source is directed to the sample, and the radiation induces fluorescent light in the sample. Each linear array includes a plurality of fused silica optical fibers that receive the fluorescent light and transmits a fluorescent light signal from the first end to an optical end port of the linear array. An end port assembly having a photo-detector is optically coupled to the optical end port. The photo-detector detects the fluorescent light signal and converts the fluorescent light signal into an electrical signal.

17 Claims, 5 Drawing Sheets

FIBER OPTICAL ASSEMBLY FOR FLUORESCENCE SPECTROMETRY

REFERENCE TO PRIOR APPLICATION

This application claims the benefit of U.S. Provisional Application No. 60/748,523, filed Dec. 7, 2005.

STATEMENT REGARDING FEDERAL RIGHTS

This invention was made with government support under Contract No. DE-AC 52-06 NA 25396, awarded by the U.S. Department of Energy. The government has certain rights in the invention. This invention further was made with support from grant number DAMD17-03-1-0368, awarded by the Army Medical Research and Material Command, and grant number HL063837, awarded by the National Heart Lung Blood Institute.

BACKGROUND OF INVENTION

The present invention relates generally to an apparatus and method for improved optical geometry for enhancement of fluorescence and spectroscopic detection in fluids. More particularly, the invention relates to an apparatus and method of fluorescence detection in fluids of marker proteins and analytes.

The conventional method of performing laser induced fluorescence measurements is to use a small transparent laboratory vessel known as a cuvette to contain the sample to be analyzed. A standard cuvette has dimensions of 1 cm×1 cm and is about 3.5 cm in height and sealed at the bottom. The cuvette is usually made of fused quartz or optical quality borosilicate glass. The cuvette is optically polished and sometimes has an antireflective coating. The cuvette is filled from an upper, open end that is usually equipped with a ground-in glass stopper.

To perform a measurement, the cuvette is filled with the liquid to be investigated and then illuminated with a laser focused through one of the cuvette's faces. A lens is placed in line with one of the faces of the cuvette located at ninety degrees from the input window to collect the laser-induced fluorescence light. Only a small volume of the cuvette is actually illuminated by the laser. This small volume produces fluorescence once affected by the laser, which is detrimentally reduced by the fact that the lens only picks up approximately ten percent of the fluorescence signal because of solid angle considerations. This is the current state of the art. It has been used for at least seventy-five years; even before the laser existed when conventional light sources were used to excite the fluorescence.

SUMMARY OF INVENTION

The present invention solves the problem of low collection efficiency as embodiments collect nearly all of the fluorescence light produced from the sample that is analyzed. This is an advance in the state of the art as it increases the amount of fluorescence signal by approximately a factor of ten over conventional apparatus.

Accordingly, one aspect of the invention is to provide a system for analyzing a sample for the presence of an analyte in a sample. The system comprises: a sample holder for containing the sample; an excitation source in optical communication with the sample, wherein radiation from the excitation source is directed to the sample, and wherein the radiation induces fluorescence in the sample, wherein the fluorescence generates fluorescent light; and at least one linear array radially disposed about the sample holder. Each linear array comprises: a first end disposed in proximity to the sample holder and an optical end port distal from the first end; a plurality of fused silica optical fibers extending from the first end to the optical end port, wherein the plurality of fused silica optical fibers receives the fluorescent light and transmits a fluorescent light signal from the first end to the optical end port of the linear array; and an end port assembly optically coupled to the optical end port, the end port assembly comprising a photo-detector, wherein the photo-detector detects the fluorescent light signal and converts the fluorescent light signal into an electrical signal.

Another aspect of the invention is to provide a linear array for detecting a fluorescent light signal from a sample. The linear array comprises: a first end and an optical end port distal from the first end, wherein the optical end port is optically polished, and wherein the first end is disposable in proximity to the sample; a plurality of fused silica optical fibers extending from the first end to the optical end port, wherein the plurality of fused silica optical fibers has an optical acceptance angle that permits the fluorescent light signal to be intercepted by the plurality of fused silica optical fibers, and wherein the plurality of fused silica optical fibers receives the fluorescent light signal and transmits the fluorescent light signal from the first end to the optical end port of the linear array; and an end port assembly optically coupled to the optical end port, the end port assembly comprising a photo-detector, wherein the photo-detector detects the fluorescent light signal and converts the fluorescent light signal into an electrical signal, and at least one of a lens and an optical filter.

A third aspect of the invention is to provide a system for detecting and analyzing an analyte in a sample. The system comprises: a sample holder for containing the sample; an excitation source in optical communication with the sample, wherein radiation from the excitation source is directed to the sample, and wherein the radiation induces fluorescence in the sample, wherein the fluorescence generates fluorescent light; and at least one linear array radially disposed about the sample holder. Each of the at least one linear array comprises: a first end disposed in proximity to the sample holder and an optical end port distal from the first end, wherein the optical end port is optically polished, and wherein the first end is disposed in proximity to the sample; a plurality of fused silica optical fibers extending from the first end to the optical end port, wherein the plurality of fused silica optical fibers has an optical acceptance angle that permits the fluorescent light signal to be intercepted by the plurality of fused silica optical fibers, and wherein the plurality of fused silica optical fibers receives the fluorescent light signal and transmits the fluorescent light signal from the first end to the optical end port of the linear array; and an end port assembly optically coupled to the optical end port, the end port assembly comprising a photo-detector and at least one of a lens and an optical filter, wherein the photo-detector detects the fluorescent light signal and converts the fluorescent light signal into an electrical signal. The system also includes an analyzer electrically coupled to the photo-detector, wherein the analyzer receives the electrical signal from the photo-detector and analyzes the sample for the presence of the analyte based upon the electrical signal.

A fourth aspect of the invention is to provide a method of analyzing a sample for the presence an analyte. The method comprises the steps of: providing a sample comprising the analyte to a sample holder; radially disposing at least one linear array around the sample holder such that a first end of the at least one linear array is disposed in proximity to the sample holder; directing radiation from an excitation source to the sample, wherein the radiation causes the sample to generate a fluorescent light signal; receiving the fluorescent light signal from the sample at the first end; transmitting the fluorescent light signal to a photo-detector in the linear array; detecting the fluorescent light signal with the photo-detector; converting the fluorescent light signal to an electrical signal; and analyzing for the presence of the analyte based on the electrical signal.

These and other aspects, advantages, and salient features of the present invention will become apparent from the following detailed description, the accompanying drawings, and the appended claims.

DETAILED DESCRIPTION

Figure 1:
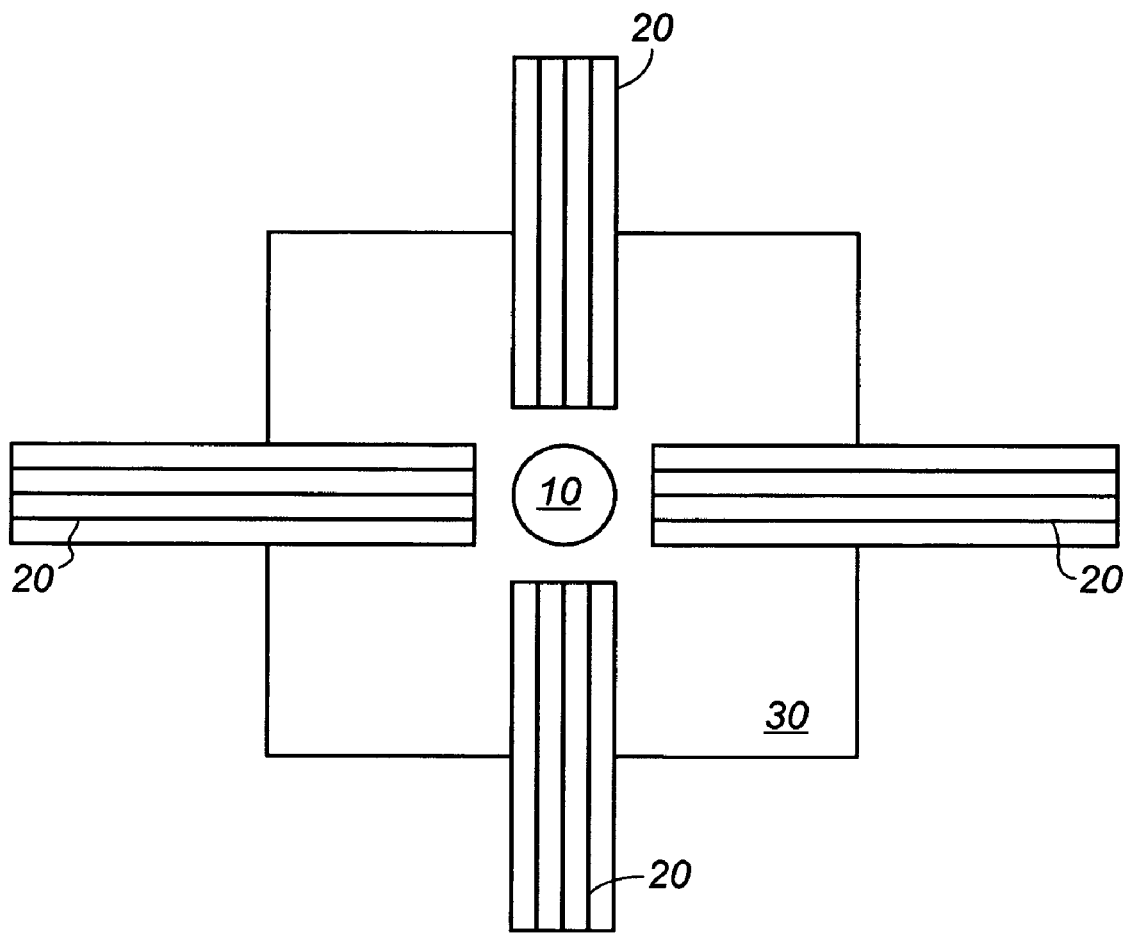
FIG. 1 is a schematic representation showing sample placement using four linear arrays.
Figure 2:
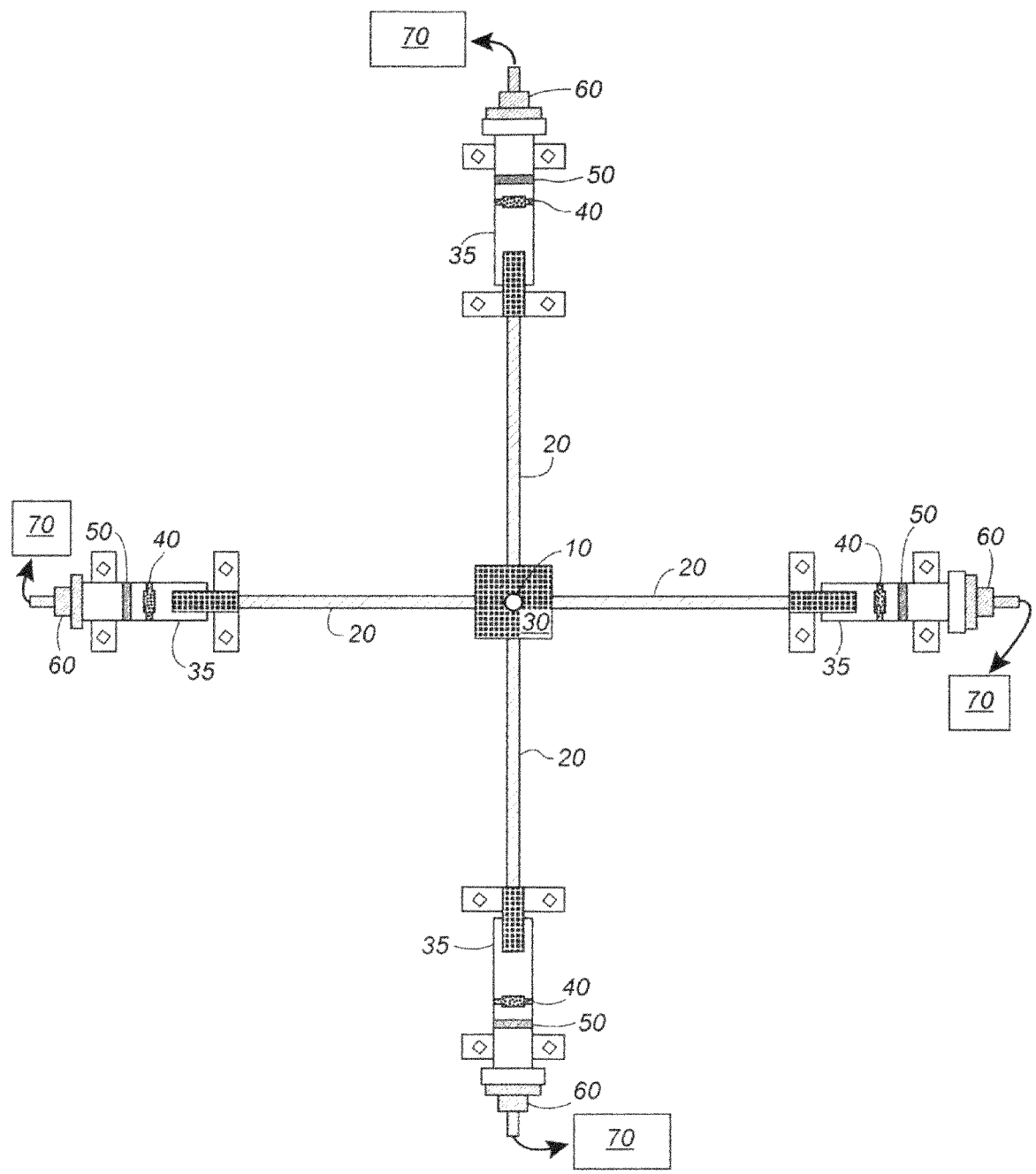
FIG. 2 is a schematic representation showing a four linear array embodiment.

In the following description, like reference characters designate like or corresponding parts throughout the several views shown in the figures. It is also understood that terms such as "top," "bottom," "outward," "inward," and the like are words of convenience and are not to be construed as limiting terms. In addition, whenever a group is described as either comprising or consisting of at least one of a group of elements and/or combinations thereof, it is understood that the group may comprise or consist of any number of those elements recited, either individually or in combination with each other.

Referring to the drawings in general and to FIG. 1 in particular, it will be understood that the illustrations are for the purpose of describing a particular embodiment of the invention and are not intended to limit the invention thereto.

The present invention is a spectroscopic—or light gathering—apparatus and corresponding method for rapidly detecting and analyzing analytes in a sample. The sample is irradiated by an excitation source in optical communication with the sample. The excitation source may include, but is not limited to, a laser, a flash lamp, an arc lamp, a light emitting diode, or the like. Irradiation of the sample causes the sample to fluoresce or scatter light. Types of light scattering that may occur include Rayleigh scattering, Raman scattering, Mie scattering, or the like. The fluoresced or scatted light corresponds to the presence and concentration of the analyte in the sample.

In one embodiment, the invention is used for detecting and analyzing analytes in either a fluid or a supporting media such as, for example, a gel. Examples of such supporting media include agarose or acrylamided gel. In another embodiment, the invention is capable of detecting and analyzing analytes in a self-supporting sample such as, a thin solid, a needle- or whisker-like crystal, or the like. In particular, the present invention may be used to rapidly detect the abnormal form of the prion protein $PrP^{sc}$ (from the normal form, PrPc) in samples of bodily fluids such and blood or urine. $PrP^{sc}$ is the marker protein used in diagnostics for transmissible spongiform encephalopathies, examples of which include bovine spongiform encephalopathy in cattle, scrapie in sheep, and Creuzfeld-Jakob disease in humans. Currently, there is no rapid means or techniques for the ante mortem determination of the presence of $PrP^{sc}$ in the dilute quantities in which it usually appears in bodily fluids. The present invention has the advantage of requiring little sample preparation and allows for electronic diagnostic equipment to be placed outside of the containment area.

Referring now to FIG. 1, one embodiment of the present invention uses four linear arrays 20 of fiber optical elements disposed at 90 degrees to each other around sample fluid 10. Arrays 20 are located radially around central frame 30, which is drilled to accept a capillary tube that holds sample fluid 10. Note that the use of four linear arrays is one particular embodiment. However, the apparatus will work with any number of arrays, with the fluorescence collection efficiency from sample fluid 10 rising correspondingly with the number of arrays added.

Each one of linear arrays 20 comprises fused silica fibers. In one embodiment, 45 silica fibers, each having a diameter of approximately 150 micrometers and a length of approximately 40 centimeters, were used. Note that the length of the linear array 20 may be varied with no practical limitation, as the material selection for the fibers is determined by a low optical absorption (attenuation) of the fluorescence produced in sample fluid 10. This feature allows for sample fluid 10 to be located in another room or area safely away from the diagnostic equipment used to analyze the sample.

Referring now to FIG. 2, each linear array 20 is located in close proximity to sample fluid 10 on one end and is connected to optical end port assembly 35 at the opposite end. Each linear array 20 is optically polished to form a robust, high quality optical output end port. Thus, the fluoresced (also referred to herein as "fluorescence," "fluorescent light" or "fluorescent light signal") or scattered light that is incident on array 20 from sample fluid 10 is transmitted through the fibers to optical end port assembly 35. The optical acceptance angle (related to the numerical aperture) of the optical fibers in arrays 20 are chosen such that essentially the entire fluorescent light signal that exits sample fluid 10 is intercepted by the many fibers. This ensures optimum collection efficiency of the precious fluorescence photons from dilute analytes, such as $PrP^{sc}$, within sample fluids.

End port assembly 35 is a simple mounting structure that is designed to hold in alignment with one or more lenses 40, one or more optical filters 50, photo-detector 60, or at least one optically dispersive element. Note that lens 40 is optional, but is used in one particular embodiment to focus the light signal and increase detection efficiency. Filters 50 may be used to reject laser light outside of the detection bandwidth of the sample analyte of interest. Photo-detector 60 may comprise detectors such as, but not limited to: photon detectors, including photo-diode detectors, photo-multipliers, charge-coupled devices, a photon-counting apparatus, optical spectrometers; and the like. In one embodiment, the optical signal is transmitted to a spectroscopic apparatus having a dispersive element that analyzes the sample for the presence of the analyte based upon the spectral signature. Photo-detector 60 may also be optimized for the fluorescence spectral region of interest.

In one embodiment, multi-spectral analysis of the sample may be achieved by providing a plurality of linear arrays, each having a different type of photo-detector. For example, a first linear array may be coupled to a spectroscopic apparatus, an second linear array may be coupled to a photo-diode detector, a fourth linear array may be coupled to a charge-coupled device, and a fourth linear array coupled to a photomultiplier tube.

The fluorescent light signal that is captured is converted to an electrical signal by photo-detector 60 and transmitted to an analyzer (not shown), which receives the electrical signal and analyses the sample for the presence of the analyte. The analyzer may include a lock-in amplifier, which enables phase sensitive detection of the electrical signal, or any other means known in the art for analyzing electric signals generated by the different types of photo-detectors described herein. The output of the analyzer may take the form of digital data, visual data (such as an oscilloscope trace or strip charts), or the like.

Figure 3:
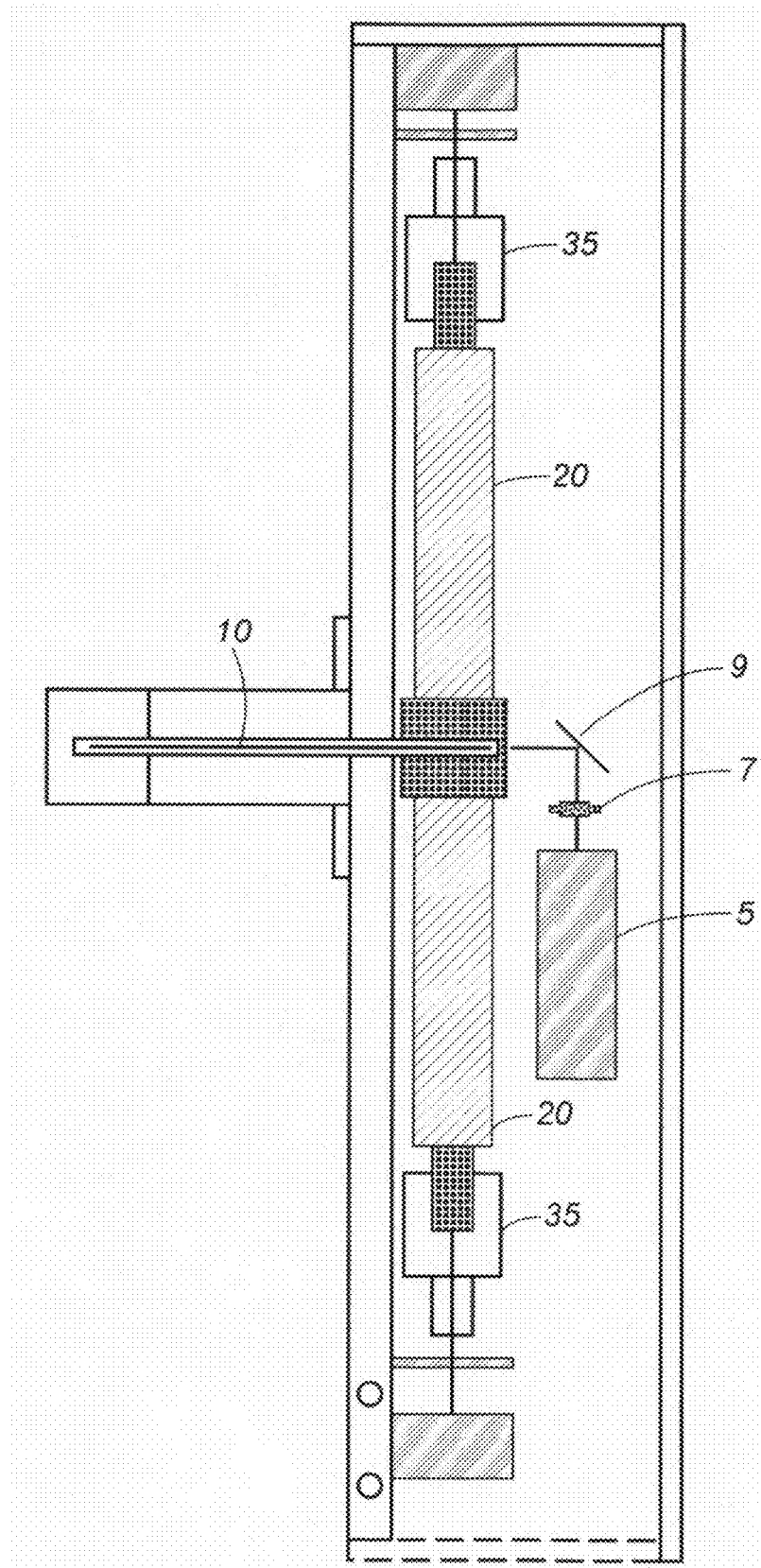
FIG. 3 is a schematic representation of a side view of a two linear array embodiment showing how a laser is focused into the sample to be analyzed.

Referring now to FIG. 3, radiation emanating from excitation source 5 is focused through lens 7 and directed off reflector 9 into sample fluid 10. Alternatively, radiation from excitation source may be directed into sample 10 through the optical fibers of at least one linear array 20. Any energy source that can excite the sample to produce fluorescence or scattered light may be used as excitation source 5. In the embodiment shown in FIG. 3, excitation source 5 is a laser that is amplitude modulated or "chopped", so that the resultant fluorescent light signal has a known modulation incorporated within. As previously mentioned, excitation source 5 may also be a flash lamp, an arc lamp, a light emitting diode, or the like. The resultant fluorescent light signals from all photo-detectors 60 may either be linearly combined for maximum amplitude or, if embodiments of two or more arrays are used, combined in quadrature to reduce common-mode noise. A phase-sensitive detector (sometimes called a "lock-in" detector), gated at the amplitude modulation frequency of excitation source 5 may be employed to further reduce electrical noise by "narrow-banding" around the selected modulation frequency.

One embodiment of a method of use includes first acquiring a sample of fluid to be investigated. This sample is loaded in a fresh 100 microliter capillary with at least 50 microliters of fluid. The capillary is then inserted into the fiber optical assembly frame, making sure that the filled section of the capillary is within the range of the fiber arrays. Then, the laser is aligned such that the output is focused into the capillary. A "chopper" (square wave amplitude modulator) reference output is then connected to the reference input of a phase sensitive detector (not shown). In this embodiment, each fiber optical array optical output port that is used is equipped with an appropriate optical filter, lens (if appropriate), and photo-detector. Each of the photo-detectors may then be connected. The photo-detectors may be connected in pairs to the quadrature input of the phase sensitive detector for noise reduction. Finally, the fluorescent light signal is then measured using the phase sensitive detector.

The advantages of such a detection array are numerous. Primarily, it permits the use of very small samples at low concentration to be optimally interrogated using the laser-induced fluorescence technique. This fiber based detection system is adaptable to existing short-pulsed detection hardware that was originally developed for sequencing single DNA molecules. The geometry is also amenable to deployment for short pulse laser single molecule detection schemes, as described below. The multi-port geometry of the system allows efficient electronic processing of the signals from each arm of the device. Finally, and perhaps most important fiber optical cables are essentially lossless for optical transmission, having an attenuation less than 10 db per kilometer). Thus, once deployed for use in a BSL3 facility, only the capillary assembly needs to be located in the facility, as the fluorescence information can be fiber optically ported to a remote location where data processing and analysis can be accomplished in an open area.

The following example illustrates the features and advantages of the invention, and are in no way intended to limit the invention thereto.

Example 1

A large area PIN diode (OSI type 10-DP/Sb, 11.28 mm diameter active area) detector was initially installed in an end port assembly with a single lens to pick up the light from the distal end of the fiber optic collector, with a notch filter to eliminate additional 532 nm laser light from a frequency doubled Nd:YAG laser. The performance of this configuration was evaluated, and it was found that the noise was too high for the intended application. The optics were then redesigned to employ basic focusing of the light onto a PIN diode (OSI type 040DP/SB, 0.81 mm diameter active area) having a much smaller area and lower noise.

Figure 4:
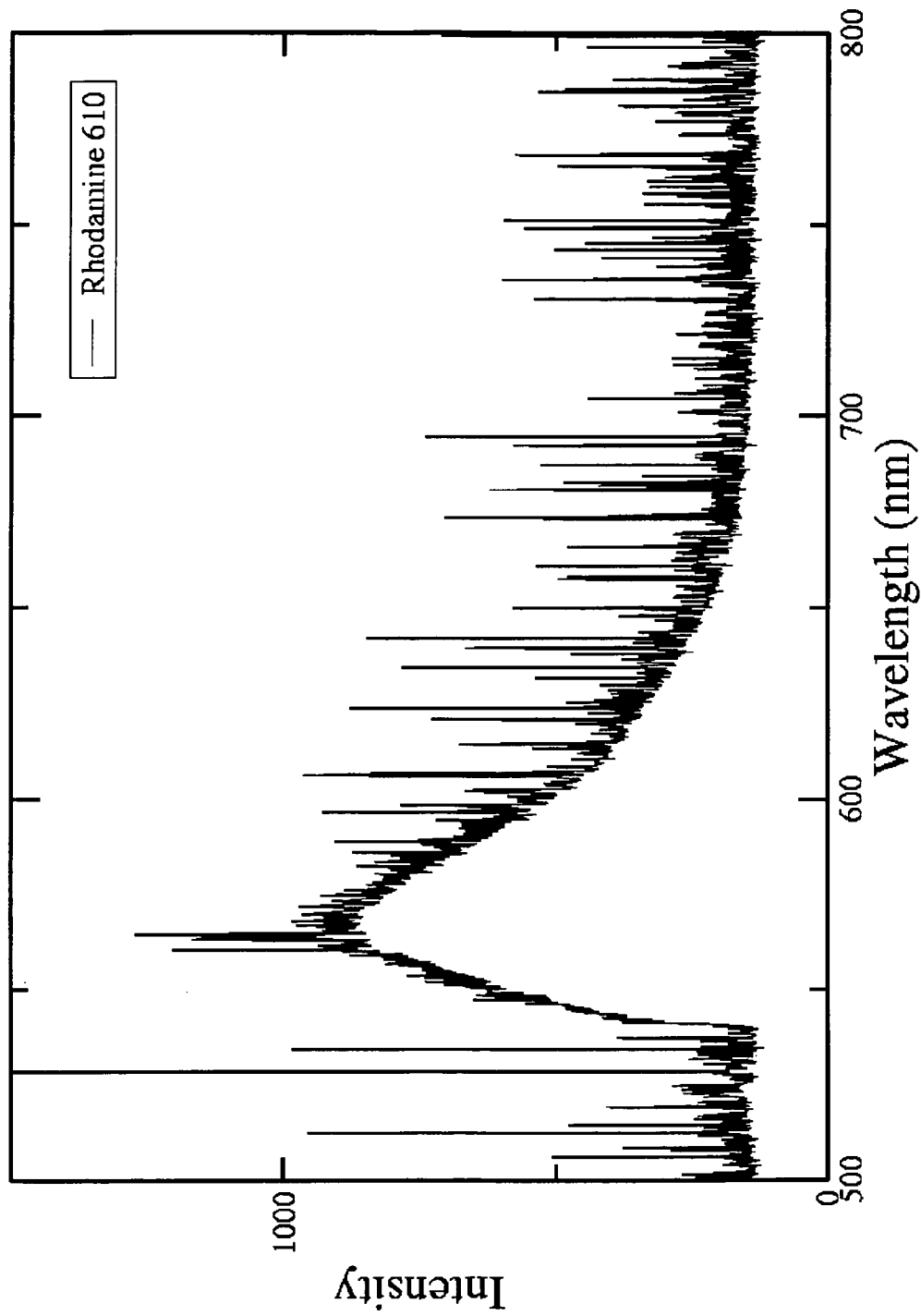
FIG. 4 is a spectrum of rhodamine 610 in water with Nd:YAG laser excitation at 532 nm.

The performance of this assembly was directly compared to the original detector using a series of measurements of dilute dye solutions. A rhodamine 610 solution having a concentration of 5 mM was prepared in reagent grade methanol. The solution was then diluted with distilled de-ionized water. Dilution curves were obtained from both detector designs on the same samples using different legs of the 4-leg fiber optic (linear array) assembly. FIG. 4 shows the spectrum of one of rhodamine 610 dilutions, obtained with a 30 mW Nd:YAG excitation source and an Ocean Optics spectrometer (Ocean Optics HR2000). The dye produces a broad fluorescence, with a peak near 570 nm. The additional sharp features seen in FIG. 4 are Raman peaks associated with the plastic sample vial. This dye is similar to Texas Red dye.

The entire fluorescence band was used for dilution measurements, although in final practice an optical band pass filter would be used to minimize interference from protein auto-fluorescence. The detectors were attached to a Stanford Research Systems RS830 DSP lock-in amplifier, and measurements were made in differential mode (common-mode noise rejection, A-B).

Control measurements were made using distilled, de-ionized water in 100 ml micro-pipettes. These showed no apparent signal (~0.1 mV with no phase-lock on the lock-in amplifier) on the new detector assembly, whereas a small (~5 mV) signal on the large area PIN diode assembly (with defined phase-lock of the signal by the lock-in amplifier) was observed. The latter indicated that a small amount of scattered laser light was leaking past the blocking filter or was at high enough angle of incidence to pass through the filter.

Figure 5:
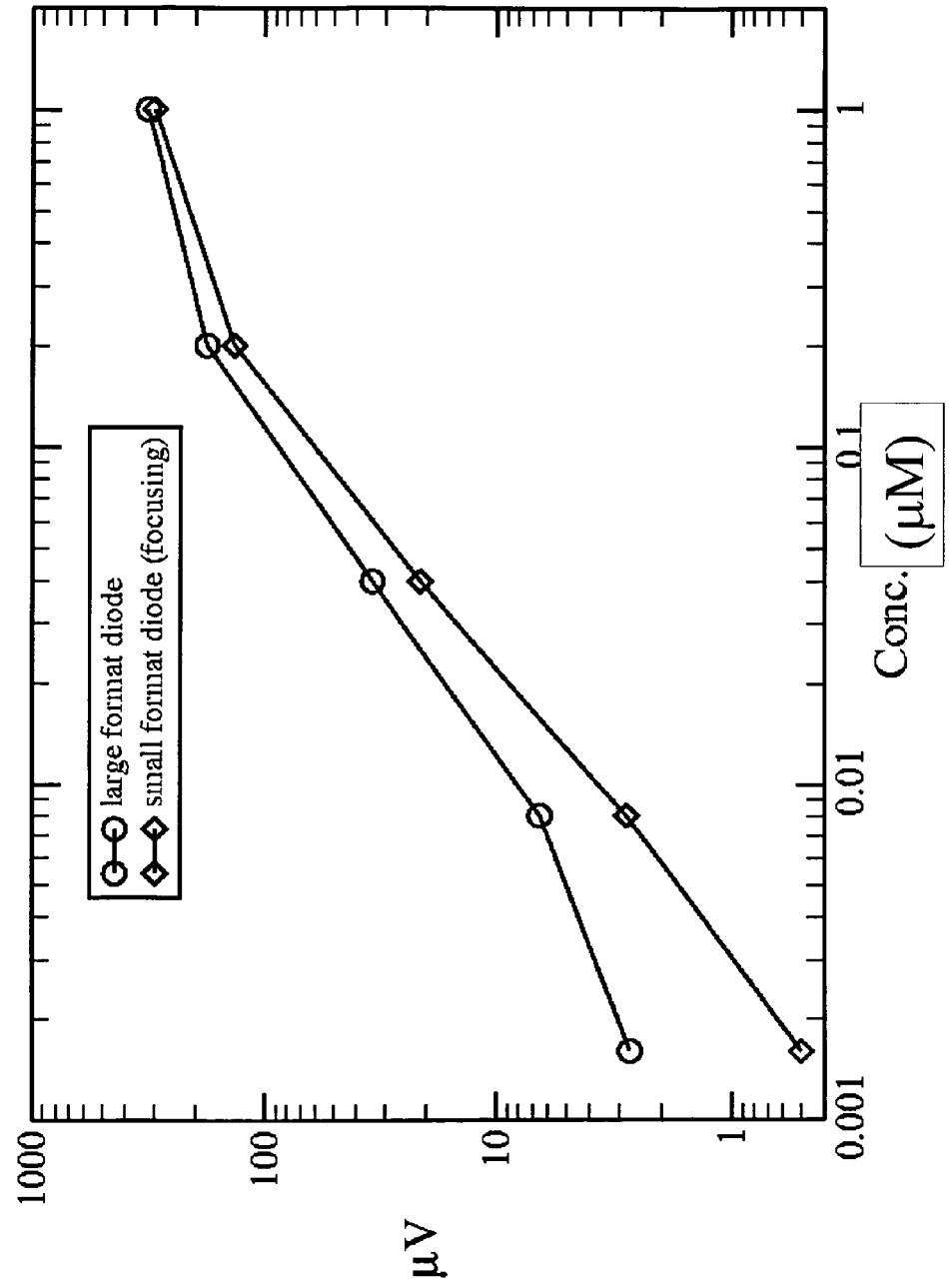
FIG. 5 is a single detector dilution measurement of rhodamine 610 in distilled water.

Samples were prepared by diluting the 5 mM solution of rhodamine 610 in methanol with distilled de-ionized water with five-fold serial dilution. Samples were loaded into 100 ml micro-pipettes and measurements made with each detector on the same sample. The excitation source for these measurements was a 30 mW Nd:YAG laser modulated with a chopper at 115 Hz (Signal Recovery Inc. model 651 chopper). FIG. 5 shows the results of the dilution measurements for comparison of detector performance. The signal from the original large format diode detector is consistently higher, although not by a factor of ten, which is the difference in active area between the two detectors. This indicates that most of the light is being gathered with the newer focusing optics and the small area diode. It also indicates that the small area diode is either being over-filled or some fine focus is needed on the small area detector. Both detectors give low measurements at 1 μM concentration, indicating the sample is optically dense at this concentration. The response is reasonably linear for both detectors down to the 10 μM concentration level, below which the large format detector becomes dominated by scattered light. The small area detector response remains linear down to the 1 μM concentration range. Ganging of four of these detectors as in the final design may make measurement to the nano-molar range possible.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

The invention claimed is:

1. A system for, analyzing a sample for the presence of an analyte in a sample, the system comprising:
   a. a sample holder for containing the sample;
   b. an excitation source in optical communication with the sample, wherein radiation from the excitation source is directed to the sample, and wherein the radiation induces fluorescence in the sample, wherein the fluorescence generates fluorescent light; and
   c. a plurality of linear arrays radially disposed about the sample holder, wherein the plurality of linear arrays consists of four linear arrays, each arranged in a planar array, wherein adjacent linear arrays are oriented 90 degrees with respect to each other, and wherein each of the at least one linear array comprises:
      i. a first end disposed in proximity to the sample holder and an optical end port distal from the first end;
      ii. a plurality of fused silica optical fibers extending from the first end to the optical end port and wherein the plurality of fused silica optical fibers receives the fluorescent light and transmits a fluorescent light signal from the first end to the optical end port of the linear array; and
      iii. an end port assembly optically coupled to the optical end port, the end port assembly comprising a photo-detector, wherein the photo-detector detects the fluorescent light signal and converts the fluorescent light signal into an electrical signal.

2. The system according to claim 1, further comprising an analyzer electrically coupled to the photo-detector, wherein the analyzer receives the electrical signal from the photo-detector and analyzes the sample for the presence of the analyte based upon the electrical signal.

3. The system according to claim 1, wherein the photo-detector comprises a spectroscopic apparatus.

4. The system according to claim 1, wherein the excitation source is a laser.

5. The system according to claim 4, wherein the laser is amplitude modulated.

6. The system according the claim 5, wherein the analyzer is a phase-sensitive detector.

7. The system according to claim 1, wherein the end port assembly further comprises at least one optical filter, wherein the at least one optical filter rejects radiation from the excitation source that is outside a detection bandwidth of a pre-determined analyte.

8. The system according to claim 1, wherein the end port assembly further comprises at least one lens, wherein the at least one lens focuses the fluorescent light signal.

9. The system according to claim 1, wherein the photo-detector is one of a photo-diode and a photo-multiplier.

10. A system for detecting and analyzing an analyte in a sample, the system comprising:
    a. a sample holder for containing the sample;
    b. an excitation, source in optical communication with the sample, wherein radiation from the excitation source is directed to the sample, and wherein the radiation induces fluorescence in the sample, wherein the fluorescence generates fluorescent light; and
    c. a plurality of linear arrays radially disposed about the sample holder, wherein the plurality, of linear arrays consists of four linear arrays, each arranged in a planar array, wherein adjacent linear arrays arc oriented 90 degrees with respect to each other, and wherein each of the at least one linear array comprises:
       i. a first end disposed in proximity to the sample holder and an optical end port distal from the first end, wherein the optical end port is optically polished, and wherein the first end is disposed in proximity to the sample;
       ii. a plurality of fused silica optical fibers extending from the first end to the optical end port, wherein the plurality of fused silica optical fibers has an optical acceptance angle that permits the fluorescent light signal to be intercepted by the plurality of fused silica optical fibers, and wherein the plurality of fused silica optical fibers receives the fluorescence signal and transmits the fluorescent light signal from the first end to the optical end port of the linear array; and
       iii. an end port assembly optically coupled to the optical end port, the end port assembly comprising a photo-detector, wherein the photo-detector detects the fluorescent light signal and converts the fluorescent light signal into an electrical signal, and at least one of a lens and an optical filter; and
    c. an analyzer electrically coupled to the photo-detector, wherein the analyzer receives the electrical signal from the photo-detector and analyzes the sample for the presence of the analyte based upon the electrical signal.

11. The system according to claim 10, wherein the photo-detector comprises a spectroscopic apparatus.

12. The system according to claim 10, wherein the excitation source is a laser.

13. The system according to claim 12, wherein the laser is amplitude modulated.

14. The system according the claim 10, wherein the analyzer is a phase-sensitive detector.

15. The system according to claim 10, wherein the end port assembly further comprises at least one optical filter, wherein the at least one optical filter rejects radiation from the excitation source that is outside a detection bandwidth of a pre-determined analyte.

16. The system according to claim 10, wherein the end port assembly further comprises at least one lens, wherein the at least one lens focuses the fluorescent light signal.

17. The system according to claim 10, wherein the photo-detector is one of a photo-diode and a photo-multiplier.

* * * * *